(12) United States Patent
Laub et al.

(10) Patent No.: US 6,635,484 B1
(45) Date of Patent: Oct. 21, 2003

(54) STANDARD USED IN DIAGNOSTIC AND/OR QUANTIFICATION TESTS

(75) Inventors: Ruth Laub, Brussels (BE); Jean Duchateau, Horrues (BE); Mario Giambattista, Braine-le-Comte (BE)

(73) Assignees: Universite Libre de Bruxelles, Brussels (BE); S.C.R.L. Department Central de Fractionnement de la Croix-Rouge, Brussels (BE)

( * ) Notice: Subject to any disclaimer, the term of this patent is extended or adjusted under 35 U.S.C. 154(b) by 0 days.

(21) Appl. No.: 09/455,990

(22) Filed: Dec. 7, 1999

(30) Foreign Application Priority Data

Dec. 7, 1998 (BE) .......................................... 09800882

(51) Int. Cl.$^7$ ........................ G01N 31/00; G01N 33/53
(52) U.S. Cl. ............... 436/8; 436/16; 435/7.1; 435/7.2; 435/7.34; 435/36
(58) Field of Search ............... 436/8, 16, 513, 436/536; 435/4, 7.1, 7.2, 7.34, 29, 34, 36

(56) References Cited

U.S. PATENT DOCUMENTS

| | | | |
|---|---|---|---|
| 4,082,734 A | * 4/1978 | Stephan | 530/390.5 |
| 4,857,451 A | * 8/1989 | Schwartz | 435/7.24 |
| 5,505,945 A | * 4/1996 | Gristina et al. | 424/164.1 |
| 5,798,267 A | * 8/1998 | Harasymiw | 436/9.7 |
| 5,808,000 A | * 9/1998 | Mannhalter et al. | 530/387.1 |

FOREIGN PATENT DOCUMENTS

| | | | |
|---|---|---|---|
| EP | 787989 | * | 8/1997 |

OTHER PUBLICATIONS

Hazlewood et al., *Clinical and Experimental Immunology*, vol. 93, pp. 157–164, 1993.*

Mahoney et al. *Human Immunology*, vol. 60, pp. 492–499, Jun. 1999.*

Kao et al. *Transplantation*, vol. 55, No. 1, pp. 192–196, Jan. 1993.*

Liu et al. *Transfusion*, vol. 37, pp. 732–736, Jul. 1997.*

Sasaki et al. *Microbiology and Immunology*, vol. 31, (6), pp. 521–530, 1987.*

Gjesing et al. *Allergy*, vol. 41 (1), pp. 51–56 (abstract), 1986.*

Klein et al. *Therapie*, vol. 48, No. 2, pp. 97–103, (abstract) 1993.*

Kotitschke et al. *Progress in Clinical and Biological Research*, vol. 337, pp. 399–401 (abstract), 1990.*

Quataert et al., "Assignment of Weight–Based Antibody Units to a Human Antipneumococcal Standard Reference Serum, Lot 89–S," *Clinical and Diagnostic Laboratory Immunology*, Sep. 1995, p. 590–597.

Coughlin et al., "Characterization of pneumococcal specific antibodies in healty unvaccinated adults," *Vaccine*, 1998, vol. 16, No. 18, p. 1761–1767.

Sørensen, "Pneumococcal polysaccharide antigens: capsules and C–polysaccharide," *Danish Medical Bulletin*, Feb. 1995, vol. 42, No. 1, p. 47–53.

National Institute for Biological Standards and Control, *Catalogue of Biological Standards and Reference Materials.*, date unknown.

* cited by examiner

*Primary Examiner*—Maureen M. Wallenhorst
(74) *Attorney, Agent, or Firm*—Merchant & Gould P.C.

(57) ABSTRACT

The present invention relates to a device for diagnosing and/or quantifying antibodies present in a biological fluid from a patient and which are specific for a reaction associated with an infection with a microorganism, specific for an autoimmune reaction or specific for an allergy. This device includes as a standard a biological sample selected from a pool of blood plasmas from more than 200 healthy patients.

8 Claims, 1 Drawing Sheet

STANDARD USED IN DIAGNOSTIC AND/OR QUANTIFICATION TESTS

OBJECT OF THE INVENTION

The present invention relates to a standard incorporated into diagnostic and/or quantification tests for antibodies resulting from an infection with a bacterial or viral agent or resulting from an autoimmune or allergic reaction.

State of the Art and Technological Background Underlying the Invention

The reference materials and standards in the biological field are preparations of substances which have a complex molecular composition involved in quality-control, diagnostic and research mechanisms.

For the diagnosis of the bacterial agents responsible for various infections affecting mammals, including man, various methods have been proposed for obtaining a standardized reference in such a diagnosis.

The agencies dealing with the reimbursement of medical expenses (INAMI) specify that a quantification of immunoglobulins, in particular the quantification of a hypogammaglobulinemia, is distinguished when the total content of immunoglobulins is less than the laboratory standard value. This standard value must be calculated as two measurable standard deviations below the mean associated with controls on the basis of the age bracket or the 95% confidence interval of a control population coupled with age. Consequently, the distinction in a test of diagnosis or quantification of a certain type of antibodies possibly directed against a bacterial agent, must be carried out relative to a standard which is constituted from the laboratory standard value. Consequently, these standards vary very greatly from one laboratory to another, which can falsify the results.

Quataert et al. ((*Clinical and Diagnostic Laboratory Immunology* Vol. 2 No. 5, pp. 590–597 (September 1995)) describe a method for identifying antibodies specific to each of the serotypes of *S. pneumoniae*. However, the standard reference batch proposed is obtained from a pool of 17 adults vaccinated with a vaccine preparation, who can present between them an excessive variance, and will necessitate the use of particularly complex mathematical extrapolations for the diagnosis of this bacterial infection. Furthermore, a cross-reactivity between the various capsular antigens of the different serotypes may arise (Coughlin et al., Vaccine 16, No. 18, p. 1761–1767, 1998).

AIMS OF THE INVENTION

The present invention is directed toward providing an improved standard in diagnostic devices, which is claimed not to have the drawbacks of the prior art, and which can be used to improve the diagnosis, quantification and/or monitoring of immune reactions resulting from infections affecting mammals, including man, in particular resulting from infections by a bacterial or viral agent or resulting from an autoimmune or allergic reaction:

One specific aim of the present invention is to provide a standard in a diagnostic device, which would be of a simple and inexpensive design and which would allow simplification of the diagnosis of such infections without making it necessary to use modifications of the operating protocols for the diagnoses usually used, and more particularly which would not make it necessary to use complex mathematical extrapolations.

CHARACTERISTIC ELEMENTS OF THE INVENTION

Figure 1:
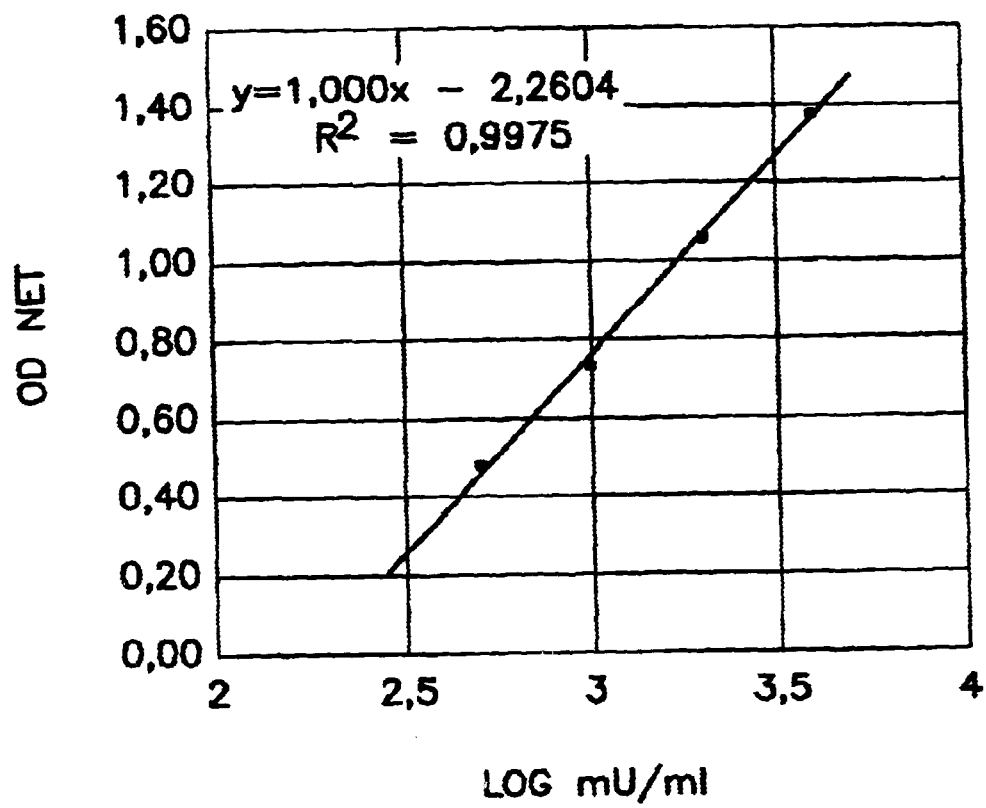
FIG. 1 is a calibration curve of the optical density of plasma pool dilutions vs. the logarithm of the corresponding anti-pneumococcal titer.

The present invention relates to a device for diagnosing and/or quantifying (including monitoring or surveillance) an immune reaction, a feature of which is the presence of antibodies of a certain type, which may be associated with an infection such as a bacterial or viral infection or a reaction of autoimmune or allergic type, in particular a food allergy, liable to affect a patient, in particular a mammal (including man).

The device of the invention makes it possible to detect and/or quantify antibodies present in a biological fluid extracted from said patient, such as a blood sample from said patient, said antibodies being directed against the agent responsible for the infection or portions thereof (in particular polysaccharide C present on the wall of bacteria) or indicating an immune or allergic reaction, a feature of the device of the invention being that it comprises, as a standard (also referred to hereinbelow as a "reference" or "calibrator"), a biological sample comprising a predefined titer of antibodies selected from a pool (i.e. a mixture) of blood plasmas obtained from more than 200 patients or healthy individuals.

The term "patient" means any mammal, including man, liable to be infected with said microorganism responsible for this infection or showing an allergic or autoimmune reaction, and capable of producing antibodies directed specifically against said microorganism or capable of presenting antibodies associated with this autoimmune or allergic reaction.

The expression "healthy patient (or individual)" means a patient who has been in contact with said microorganism responsible for said infection and who does not exhibit or no longer exhibits said infection. For example, the expression "healthy patients (or individuals)" would be understood to refer to healthy adults of a population exposed, even transiently, to a bacterial infection, in particular with *Streptococcus pneumoniae*, and possessing antibodies of anti-*Streptococcus pneumoniae* type. Consequently, a mixture of plasmas or of sera from healthy patients (or individuals), i.e. from patients or individuals with little or no probability of exhibiting said infection, can serve as a standard.

The inventors have noted that if the biological sample prepared from such a pool, i.e. a mixture of plasmas, produced from more than 200 patients, preferably when the number of patients exceeds 1000, 2000 or even 5000 healthy patients, will be distinguished by a very low (statistical) variance and will be able to serve as a "universal" standard for diagnostic and/or quantification devices, since they will be distinguished by a very low variance, even if, in said plasma pool, one or more of the healthy patients or individuals had, at the time of the blood donation, said infection which it is desired to distinguish. Specifically, the titer of these antibodies relative to the number of antibodies selected from other adults characterized as healthy patients or individuals, would not significantly affect the advantageous properties of the standard of the invention.

In addition, the standard or calibrator of the invention can advantageously be [lacuna] from a low-temperature supernatant of said plasma pool, which may be readily available in large amount.

Such a standard not only allows diagnosis but also quantification (calculation of the antibody titer) as well as monitoring (also referred to as "surveillance") of said immune reaction. This monitoring is particularly useful when it is desired to see the evolution of a vaccination with respect to a microorganism responsible for an infection, or with respect to an anti-allergic treatment or intended for the treatment of a pathology or an autoimmune syndrome.

The standard or reference of the invention, which will consist of a predefined titer of antibodies distinguished by a low variance, i.e. by a significant difference between the antibody types, allows the ready use of such a standard in a diagnostic and/or quantification device without the need for any extrapolations or complex mathematical analyses and without affecting the usual procedures of diagnosis, quantification and, optionally, monitoring mentioned above. Such a standard can advantageously be used in any type of diagnostic or quantification device, in particular in any type of diagnostic and/or quantification kit based on the ELISA technologies as described below, or other technologies for detecting antibodies such as the RIA or hemagglutination technologies, and on any type of support.

The device and the process of the invention can also include a medium and a step for preincubating the samples to be tested, preferably in the presence of polysaccharide C, advantageously of about 2.5 $\mu$m/ml of polysaccharide C for a period of 30 min at 37° C., to assay the capsular antibodies in the various preparations of an immunochemical test using, as immobilized antigens, polysaccharide antigen preparations (for example for the diagnosis of *Streptococcus pneumoniae*).

The diagnostic device of the invention is particularly suited to the diagnosis, quantification and/or monitoring of immune reactions associated with an allergic reaction, in particular for the detection, quantification and/or monitoring of antibodies of IgG or IgE type associated with an allergic reaction, in particular food allergic reactions, for the detection of auto-antibodies in the case of an autoimmune reaction or for the detection, quantification and/or monitoring of antibodies directed against various bacterial or viral infections, in particular infections with strains of *Streptococcus pneumoniae*, Neisseria and Hemophilus.

The subject of the invention will be described in detail, and with no limitation being implied, in the implementation example below.

EXAMPLE 1

ELISA Immunoenzymatic Test for the Detection of Anti-pneumococcus Anti-bodies in Plasma, Plasma Pools and Immunoglobulin Concentrates The *Streptococcus pneumoniae* strain is a common host of the oro-pharyngeal flora, the capsule of which imparts the virulence and the antigenicity. The antibodies raised against the polysaccharide antigens of the capsule are protectors of the infection. The level of *Streptococcus pneumoniae* carriers varies according to age, the season and the infectious or non-infectious environment. Pneumococci are the major cause of the pneumonias acquired in communities and the frequent source of acute otitis of the middle ear, sinusitis and pharyngitis. Pneumonias, which are brought about in the majority of cases by pneumococci, are reported as being the fifth most common cause of death in the United States. In Belgium, the incidence of pneumococcal infections is 200,000 cases a year. The level of antibiotic-resistant strains is constantly on the increase, 12% being resistant to tetracycline and 21% to erythromycin. The death rate is estimated at 2000 deaths a year, which appear to be associated with problems of resistance to antibiotics.

Although pneumococci affect all individuals (70% of healthy carriers), certain terrains are predisposed to pneumococcal infection, such as age, broncho-pneumopathies, cancers of the upper sero-digestive pathways, alcoholism and nicotine addiction, as well as cardiac insufficiency. Hypoasplenia represents a certain aggravating factor, as does hemopathy which particularly affects children less than 5 years old.

The search for anti-pneumococcal antibodies in the plasma and the derived fractions by means of the diagnostic kit of the invention make it possible to detect the anti-capsule polysaccharide antibodies of the 23 most common serotypes (95% of the strains isolated in Belgium). The ELISA immunoenzymatic test described below allows the quantitative assay of anti-pneumococcal antibodies in a plasma or a plasma fraction without pretreating the plasma sample harvested on anticoagulants. This makes it possible to detect the antibodies in plasmas or plasma fractions containing few antibodies (concentration 1000 times less than the average encountered in healthy individuals) as well as in hyperhuman plasmas obtained after vaccination.

The device of the invention thus allows particularly effective monitoring (or surveillance) of a vaccination or of the development of an infection.

Preparation of the Solutions, Dilutions and Samples

Solution A: 10×concentrated PBS buffer
400 g NaCl
10 g KCl
72 g $Na_2HPO_4$
12 g $KH_2PO_4$
Make up to 5 liters with mQ water.
Solution B: Washing solution (1×PBS-0.1% Tween)
The final concentrations are, respectively:
0.14 M NaCl
2.7 mM KCl
10 mM $Na_2HPO_4$
1.8 mM $KH_2PO_4$
0.1% Tween 20
For 1000 ml of working solution, take:
100 ml of solution A
1 ml of Tween 20
899 ml of mQ water.
Solution C: Buffer for diluting the peroxidase-labeled antibody
Solution $C_0$: 5% bovine albumin stock solution
For 10 ml of solution:
500 mg of BSA (Sigma)
Make up to a final volume of 10 ml with mQ water. The solution is stored at 20° C.
Working solution C:
For 10 ml of solution C:
1 ml of solution $C_0$
1 ml of solution A
8 ml of mQ water
Solution D: Solution for saturating and diluting the samples to be assayed
  dissolve 20 g of casein (Merck) in 400 ml of mQ water
  heat to 60° C. and adjust the pH regularly to 9.6 with 5M NaOH mix while heating at 60° C. for 2 h on a magnetic stirrer add 36 g of NaCl and 0.8 g of Thimerosal (Merck)

add slowly 1600 ml of mQ water and 200 ml of 20 mM Tris-HCl, pH 6.6. (Merck)

adjust the pH to 7.2–7.4 with 1M HCl or 1M NaOH centrifuge the solution at 4500 rpm for 1 h at 22° C.

leave to decant and filter through a Whatman® filter freeze at −20° C. in 500 ml flasks filter before use through a Milli-Fil PF® 0.8 µm filter (Millipore) and store at 4° C.

The final solution is 10 mM Tris; pH 7.2–7.4; 0.15M NaCl; 0.02% Thimerosal®; 0.5% casein.

Solution E: Solution for stopping the reaction —$H_2SO_4$: 2N

Preparation of the Calibrator Dilutions

A calibrator flask is made up in 1 ml of "ready-to-use" casein (calibrator 1/1).
Examples:
   Calibrator at 1/125: 16 µl of calibrator 1/1+1984 µl of "ready-to-use" casein
   Calibrator at 1/250: 400 µl of calibrator 1/125+400 µl of "ready-to-use" casein
   Calibrator at 1/500: 400 µl of calibrator 1/250+400 µl of "ready-to-use" casein
   Calibrator at 1/1000: 400 µl of calibrator 1/500+400 µl of "ready-to-use" casein Preparation of the Various Samples to be Tested
Examples:
   Sample No. 1 at 1/250: take 8 µl of sample to be tested+1992 µl of casein
   Sample No. 2 at 1/500: take 400 µl of sample No. 1+400 µl of casein

PROCEDURE

A. Preparation of the Pneumovax $R^{23}$ Solution for "Coating"

The antigen concentration of the Pneumovax $R^{23}$ vaccine (Pasteur Mérieux MSD) is 1.15 mg/ml. The working concentration is 1 µg/ml.
   For a plate (96 wells):
   9.85 ml of mQ water
   1.15 ml of solution A
   11 ml of Pneumovax $R^{23}$ stock solution
   Add 100 µl of the antigen solution at 1 µg/ml into each well using a multipipette.
   Cover the plate with a transparent adhesive film. Incubate for 16 h at 4° C.

B. Washing the Plate

Wash the microplate 5 times with solution B using a plate washer (NUNC Immuno Wash 8).
   Shake the plate on a paper towel to dry it as much as possible.

C. Saturation of the Non-specific Sites

Add 200 µl of solution D to each well using a multipipette.
   Cover the microplate with a transparent adhesive film. Incubate for 30 min at room temperature.
   Remove the solution and dry the plate as much as possible by shaking it on a paper towel.

D. Incubation With the Sample to be Tested

During the saturation step (Step C), prepare the dilutions of the various samples to be tested.

D-1: If the Sample to be Tested is a Plasma:

All the dilutions of the samples to be tested are made in solution D.
   In order to obtain a calibration curve, it is necessary:
      to make up the standard plasma pool with 1 ml of mQ water (mix for 2 min on a vortex mixer)
      to prepare 250 µl of the standard pool plasma diluted to 1/125; 1/250; 1/500 and 1/1000 in solution D as described above
   To prepare the samples to be tested, it is necessary
      to prepare 250 µl of a 1/250 and 1/500 dilution of the plasmas to be tested in solution D
      to add "in duplicate" 100 µl of the various dilutions to be tested (calibration curve and sample)
   To prepare the blanks (these samples do not comprise any first antibody), it is necessary:
      also to add to 4 wells 100 µl of solution D "in duplicate"
      to cover the plate with a transparent adhesive film and leave it to incubate for 1 h at 37° C.

D-2: If the Sample to be Tested is an Immunoglobulin Concentrate:

Proceed as described above, by preparing 250 µl of a dilution of the batch to 0.1; 0.05; 0.025 and 0.01 mg/ml in buffer D.

E. Addition of Rabbit Antiserum Labeled With Peroxidase (HRP) and Specifically Directed Against Human IgGs Wash the plate 5 times with solution C
   Add a second antibody which is an anti-human IgG rabbit antiserum labeled with peroxidase.
   It is possible in particular to use an antibody sold by the company Sigma under the reference number A8792 at a dilution of 1/60,000 or an antibody sold by the company Dako under the reference number P0214 at a dilution of 1/28,000.
   Add 100 µl of rabbit antiserum to each well and incubate for 30 min at 37° C.

F. Revealing the Plates

The plates are revealed by adding substrate (TMB or liquid 3,3',5,5'-tetramethylbenzidine from Sigma (ref.: T8665)) brought to room temperature.
   Wash the plate 5 times with solution C
   Add 100 µl of TMB solution to all the wells
   Incubate for 15 min at 37° C.

G. Stopping the Reaction

The reaction is stopped by adding 100 µl of 0.5N $H_2SO_4$.

H. Spectrophotometric Measurement

Read the absorbance at 450 nm within 15 min.

Calculating the Anti-pneumococcal Antibody Titer

A. Establishing a Calibration Curve and Anti-pneumococcal Antibody Titer

By definition, a dilution of a standard plasma pool to 1/500 has a titer of 1000 mU/ml of anti-pneumococcal IgGs.
   The net absorbance is plotted on a graph:
   $Od_{net}$=average of the $Od_{measured}$−average of the $Od_{blanks}$ obtained for each plasma pool dilution as a function of the logarithm of the corresponding anti-pneumococcal titer. The equation of the calibration curve is determined using a linear regression progam.

B. Calculating the Titer on Unknown Samples

Using the calibration curve equation, the titer in mU/ml of anti-pneumococcal antibodies present in the unknown samples is determined, taking into account the dilutions used.

Table 1 represents the value of the densities obtained at 450 nm.

The titer for each of the dilutions is recalculated taking the dilution factor into account.

TABLE 1

| Calibrator | | Average | | Net O.D. |
|---|---|---|---|---|
| Dilution | mU/ml | O.D. | SDEV | (–blank) |
| 1/125 | 4000 | 1.665 | 0.018 | 1.591 |
| 1/250 | 2000 | 1.172 | 0.039 | 1.098 |
| 1/500 | 1000 | 0.834 | 0.006 | 0.760 |
| 1/1000 | 500 | 0.536 | 0.010 | 0.462 |
| Blank | | 0.074 | 0.011 | |

Table 2 represents the value of the densities obtained as a function of the IU/ml (logarithmic scale for the calibrator).

TABLE 2

| Calibrator | |
|---|---|
| Log mU/ml | Net O.D. |
| 3.602 | 1.591 |
| 3.301 | 1.098 |
| 3.000 | 0.760 |
| 2.699 | 0.462 |

The value of the average optical densities, corrected from the blank, are plotted on a graph as a function of the titer (semi-logarithmic scale).

The titer for the unknown samples is calculated using the calibration curve parameters (FIG. 1).

1) Equation of the calibration curve:

$$OD = a \times (\log mU/ml) - b; \text{ with } a=1.007 \text{ et } b=2.26.$$

2) Calculation of the titer of an unknown sample: calculating the log value (Titre). $\text{Log (Titre)} = Od_{(measured)} - b/a$ 3) Titre $(mU/ml) = 10^{Log(Titre)}$.

4) Calculating the average titer of the sample according to the two different dilutions used (1/250 and 1/500), taking the dilution factor into account.

EXAMPLE 2

Specificity of the Diagnostic Test With Respect to Capsular Antigens of *S.Pneumoniae*

The immune response directed against the polysaccharide antigens of *S. pneumoniae* is manifested by the presence of antibodies specific for the cell wall and the capsule (Sorensen et al., 1995 *Danish Medical Bulletin* 42, p. 47–53). These two types of antibodies can be demonstrated in particular in healthy donors, patients who have or have not been treated with immunoglobulins, or vaccinated with said immunoglobulins.

The relative determination of these two types of antibody may prove to be important, in particular for capsular anti-antigenic antibodies whose protective role against a future infection has been demonstrated (Lee et al., 1997 *Critical Reviews in Microbiology* 23 (2), p. 121–142).

Consequently, the diagnostic and/or quantification device of the invention can be used advantageously to allow the monitoring of such infections.

For the purpose of distinguishing the antibodies directed against polysaccharide C present in the bacterial wall and in the anti-pneumococcal vaccine of capsular antibodies, polysaccharide C (purified, for example, from strains lacking a capsule or obtained by genetic engineering) is used in a preliminary step in order to neutralize the antibodies specifically directed against this polysaccharide.

A preincubation of the samples to be tested, for example in the presence of 2.5 µm/ml of polysaccharide C for a period of 30 min at 37° C. makes it possible to assay the capsular antibodies in the various preparations in the immunochemical test, using, as immobilized antigens, preparations of polysaccharide antigens (obtained for example from the product Pneumovax® or from other sources of antigens).

Under these conditions, the level of capsular antibodies relative to the total antibodies is about 50% in the standard plasma pools, 80% in the standard 89SF and from 10 to 90% in healthy donors.

What is claimed is:

1. A standard material for use in detecting antibodies specific for a reaction associated with an infection with a microorganism selected from the group consisting of the strain *Streptococcus pneumoniae*, strain Neisseria and strain Hemophilus or specific for an auto immune reaction or specific for an allergy, the standard material comprising a predefined titer of the antibodies selected from a pool of blood plasmas obtained from more than 200 healthy individuals.

2. The standard material of claim 1, wherein the standard comprises a predefined titer of the antibodies selected from a pool of blood plasmas obtained from more than 1000 healthy individuals.

3. The standard material of claim 1, wherein the standard comprises a predefined titer of the antibodies selected from a pool of blood plasmas obtained from more than 5000 healthy individuals.

4. The standard material of claim 1, wherein the healthy individuals are human.

5. A kit for detecting antibodies present in a biological fluid from an individual patient, the kit comprising the standard material of claim 1.

6. The standard material of claim 1, wherein the standard material is included in a kit.

7. A method for quantifying antibodies present in a biological fluid from an individual patient, the antibodies being specific for a reaction associated with an infection with a microorganism selected from the group consisting of the strain *Streptococcus pneumoniae*, strain Neisseria and strain Hemophilus, specific for an autoimmune reaction or specific for an allergy, the method comprising:

providing the standard material according to claim 1;

subjecting serial dilutions of said standard material, in an antibody detection assay, to an antigen specific for a reaction associated with an infection with a microorganism selected from the group consisting of the strain *Streptococcus pneumoniae*, strain Neisseria and strain Hemophilus, specific for an autoimmune reaction or specific for an allergy to generate a standard curve;

subjecting said biological fluid from said individual patient, in an antibody detection assay, to an antigen specific for a reaction associated with an infection with a microorganism selected from the group consisting of the strain *Streptococcus pneumoniae*, strain Neisseria and strain Hemophilus, specific for an autoimmune reaction or specific for an allergy to generate a response; and quantifying said antibodies present in said biological fluid of said individual patient by comparing to said standard curve the response generated by said biological fluid.

8. A method for detecting an infection with a microorganism selected from the group consisting of the strain *Streptococcus pneumoniae*, strain Neisseria and strain Hemophilus, an autoimmune reaction or an allergic reaction in a patient, the method involving quantifying antibodies present in a biological fluid from the patient, the antibodies being specific for a reaction associated with the microorganism, autoimmune reaction, or allergic reaction, the method comprising:

providing the standard material according to claim 1, subjecting serial dilutions of said standard material, in an antibody detection assay, to an antigen specific for a reaction associated with an infection with a microorganism selected from the group consisting of the strain *Streptococcus pneumoniae*, strain Neisseria and strain Hemophilus, specific for an autoimmune reaction or specific for an allergy to generate a standard curve;

subjecting said biological fluid from said individual patient, in an antibody detection assay, to an antigen specific for a reaction associated with an infection with a microorganism selected from the group consisting of the strain *Streptococcus pneumoniae*, strain Neisseria and strain Hemophilus, specific for an autoimmune reaction or specific for an allergy to generate a response; and quantizing said antibodies present in said biological fluid of said individual patient by comparing to said standard curve the response generated by said biological fluid, wherein the presence of antibodies specific for the microorganism, autoimmune reaction, or allergic reaction indicates an infection by the microorganism, the presence of the autoimmune reaction, or the presence of the allergic reaction, respectively, in the individual patient.

* * * * *